(12) United States Patent
Murphy et al.

(10) Patent No.: US 7,951,538 B2
(45) Date of Patent: *May 31, 2011

(54) METHOD TO DETERMINE THE RISK FOR SIDE EFFECTS OF AN SSRI TREATMENT IN A PERSON

(75) Inventors: Greer M. Murphy, Stanford, CA (US); Alan F. Schatzberg, Los Altos, CA (US)

(73) Assignee: The Board of Trustees of the Leland Stanford Junior Univeristy, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/421,492

(22) Filed: Apr. 9, 2009

(65) Prior Publication Data

US 2010/0087421 A1 Apr. 8, 2010

Related U.S. Application Data

(63) Continuation of application No. 11/450,212, filed on Jun. 8, 2006, now abandoned, which is a continuation of application No. 10/230,832, filed on Aug. 29, 2002, now Pat. No. 7,083,921.

(60) Provisional application No. 60/315,644, filed on Aug. 29, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6; 435/91.2; 536/23.5; 536/24.31

(58) Field of Classification Search .................. None
See application file for complete search history.

(56) References Cited

U.S. PATENT DOCUMENTS 7,083,921 B2 8/2006 Murphy et al.
2006/0228750 A1 10/2006 Murphy et al.

FOREIGN PATENT DOCUMENTS

WO WO 96/17801 6/1996

OTHER PUBLICATIONS

Kato et al. Psychiatry Research. 2009. 167: 97-105.*
Lucentini et al. The Scientist, Dec. 2004, p. 20.
Oswald et al. "Lack of association between the 5HT2A receptor polymorphism (T102C) and unipolar affective disorder in a multicentric European study." European Neuropsychopharmacology (2003) 13(5):365-368.
Fehr et al. "Serotonergic polymorphisms in patients suffering from alcoholism, anxiety disorders and narcolepsy." Progress in Neuro-Psychopharmacology and Biological Psychiatry (2001) 25(5):965-982.
Du et al. "Association of Polymorphism of Serotonin 2A Receptor Gene with Suicidal Ideation in Major Depressive Disorder," American Journal of Medical Genetics (Neuropsychiatric Genetics) (2000) 96:56-60.
Chen et al. "Lack of Allelic Association Between 102T/C Polymorphism of Serotonin Receptor Type 2A Gene and Schizophrenia in Chinese," Psychiatric Genetics (1997) 7:35-38.
Murphy et al. "Pharmacogenetics of Antidepressant Medication Intolerance," Am. J. Psychiatry (2003) 160 (10):1830-1835.
Kato et al. "Effects of the serotonin type 2A, 3A and 3B receptor and the serotonin transporter genes on paroxetine and fluvoxamine efficacy and adverse drug reactions in depressed Japanese patients." Neuropsychobiology, 2006, 53: 186-195.

* cited by examiner

*Primary Examiner* — Carla Myers
(74) *Attorney, Agent, or Firm* — Paula A. Borden; Bozicevic, Field and Francis LLP

(57) ABSTRACT

A new method is found to determine an increased risk for side effects of an SSRI treatment in a person by genotyping the person for the presence of the 102 C/C DNA sequence in the 5-HT$_{2A}$ receptor gene. This provides for a method to improve the treatment of an SSRI responsive disorder and in particular depression.

13 Claims, No Drawings

METHOD TO DETERMINE THE RISK FOR SIDE EFFECTS OF AN SSRI TREATMENT IN A PERSON

CROSS-REFERENCE TO RELATED APPLICATIONS

The present application which is a continuation of U.S. application Ser. No. 11/450,212 filed Jun. 8, 2006, now abandoned which is a continuation of U.S. application Ser. No. 10/230,832 filed Aug. 29, 2002 now U.S. Pat. No. 7,083,921, which claims the benefit of Provisional Application 60/315,644 filed on Aug. 29, 2001; the disclosures of which are herein incorporated by reference in their entirety.

FIELD OF THE INVENTION

The invention relates to a method to determine the risk for side effects of an SSRI treatment in a person and to a method to improve medical treatment of a disorder, which is responsive to treatment with a selective serotonin reuptake inhibitor (SSRI).

BACKGROUND OF THE INVENTION

SSRI's are widely used for the treatment of various disorders. Major depression is the most common among those disorders treated with an SSRI. Other well-known disorders that can be treated with SSRI's are dysthymia, premenstrual dysphoric disorder, panic disorder, obsessive compulsive disorder, social phobia, post-traumatic stress disorder, generalised anxiety disorder, obesity and alcoholism (Schatzberg J. Clin Psychiatry, 61, Suppl 11: 9-17, 2000; Masand and Gupta, Harvard Rev Psychiatry, 7: 69-84, 1999). Evidence is accumulating that such drugs have also beneficial effects in less common disorders, such as trichotillomania, paraphilia and related disorders and borderline personality disorder. Benefits are also obtained with use of an SSRI in smoking cessation and in the control of addictive behavior.

It occurs regularly that a once started treatment with an SSRI fails to have clear therapeutic results or has to be discontinued due to poor tolerance of side effects. Known side effects of SSRI's are headache, nausea, appetite inhibition, agitation, sleep disturbance, and disturbance of sexual functions, such as anorgasmia and loss of libido. In practice the overall therapeutic result of a regularly applied SSRI treatment is the resultant of the improvement of the disorder and the burden of negative side effects. In view of the existence of alternatives to SSRI's for the treatment of disorders, treatment results can be improved when patients are selected for tolerance and chance of success of an SSRI. Patients at risk for negative side effects can be treated with a treatment other than a treatment with an SSRI. Consequently, it will be very useful if it were possible to predict the occurrence of cumbersome side effects of a treatment with an SSRI.

It is a known assumption that the genetic make-up of a person can contribute to the individually different responses of persons to a medicine (Roses, Nature 405:857-865, 2000). Examples of genetic factors, which determine drug tolerance, are drug allergies and severely reduced metabolism due to genetic absence of suitable enzymes. A case of a lethal lack of metabolism due to cytochrome P-450 2D6 genetic deficiency is reported by Sallee et al J Child & Adolesc. Psychopharmacol, 10: 27-34, 2000. The metabolic enzymes in the liver occur in polymorphic variants, causing some persons to metabolise certain drugs slowly and making them at risk for side effects due to excessively high plasma drug levels. Many genes that are expressed in the brain such as neurotransmitter receptors and transporter proteins have polymorphic variants. These variants may influence the interaction of a drug with cells of the brain, which may influence the frequency of drug side effects (Cravchik and Goldman, Arch Gen Psychiatry 57:1105-1114, 2000). Variants of the gene for the serotonin 2A receptor ($5\text{-HT}_{2A}$ receptor) exist, which differ in one nucleotide at location 102. Alleles with 102C and 102T exist. This particular polymorphism has been explored in attempts to find genetic predictors for schizophrenia symptomatology, suicidal ideation, alcohol dependency, bipolar affective disorder, fibromyalgia, Tourette's syndrome, and other diseases. Such attempts have met with little confirmed success thus far (Bondy et al., Am J Med Genetics, 96:831-835, 2000; Massat et al., Am J Med Genetics, 96:136-140, 2000; Serretti et al., Am J Med Genetics, 96; 84-87, 2000; Bondy et al., Neurobiol Diseases, 6:433-439, 1999; Du et al., Am J Med Genetics, 96:56-60, 2000).

SUMMARY OF THE INVENTION

Unexpectedly, it has now been found that it is possible to determine an increased risk for side effects of an SSRI treatment in a person by genotyping the person for the presence of the 102 C/C DNA sequence in the $5\text{-HT}_{2A}$ receptor gene.

This finding also enables that an improved treatment result for a disorder which is responsive to treatment with an SSRI, can be obtained by genotyping the patients for the presence or absence of said DNA sequence and selecting a therapy which diminishes the risk for side effects of an SSRI treatment.

In particular, the improvement is obtained in the treatment of depression for which it is preferred to select as therapy administering mirtazapine in an amount effective to treat depression in the person having the 102 C/C DNA sequence in the $5\text{-HT}_{2A}$ receptor gene.

DETAILED DESCRIPTION OF THE PREFERRED EMBODIMENTS

Genotyping a person for the presence of the 102 C/C DNA sequence in the $5\text{-HT}_{2A}$ receptor gene means screening patients to determine the type and number of $5\text{-HT}_{2A}$ receptor alleles present in the patient. Such screening may be carried out by nucleic acid sequencing of DNA. For example, the screening may be accomplished by restriction isotyping methods, which include the general steps of polymerase chain reaction amplification, restriction digestion, and gel electrophoresis. Screening may also be carried out by other types of nucleic acid sequencing, e.g., by hybridisation or oligotyping, or by direct sequencing of DNA nucleotides.

$5\text{-HT}_{2A}$ receptor gene means the gene (designated as HTR2A) which encodes for the serotonin $5\text{-HT}_{2A}$ receptor. The $5\text{-HT}_{2A}$ receptor gene is located on chromosome 13q14-21. At location 102 a C->T polymorphism is known with about 40% frequency of the 102T allele in a normal Caucasian population. The terms allele and gene are used interchangeably herein. The DNA and amino acid sequences of the $5\text{-HT}_{2A}$ receptor gene and the $5\text{-HT}_{2A}$ receptor itself are known and are available, e.g., at NCI nucleotide accession No. NM_000621 and protein accession No. NP_000612.

The term 102 C/C DNA sequence refers to homozygous presence of cytidine at location 102 in both alleles for the $5\text{-HT}_{2A}$-receptor. The terms 102 T/C and 102 T/T refer to the heterozygous state, and the homozygous state for thymidine at location 102 of the 5-HT$_{2A}$-receptor, respectively. The homozygous C/C genotype occurs with a frequency of about 33% in Caucasian populations (Frisch, Mol Psychiatry 4:389-392, 1999).

Side effects of an SSRI treatment are those related to SSRI treatment based on a positive correlation between frequency or intensity of occurrence and SSRI drug treatment. Such information is usually collected in the course of studies on efficacy of a drug treatment and many methods are available to obtain such data. Resulting information is widely distributed among the medical profession and patients receiving treatment. Specifically identified SSRI treatment related side effects are headache, dizziness, agitation, trouble concentrating, gastrointestinal disturbances, nausea, vomiting, diarrhea, appetite inhibition, sleep disturbance, somnolence, insomnia and disturbance of sexual functions, such as anorgasmia and loss of libido. Premature drug-related discontinuation of an SSRI treatment and drug-related adverse events are also included here within the definition of side effects of an SSRI treatment.

A treatment result is defined here from the point of view of the treating doctor, who judges the efficacy of a treatment as a group result. Within the group, individual patients can recover completely and some may even worsen, due to statistical variations in the course of the disease and the patient population. Some patients may discontinue treatment due to side effects, in which case no improvement in their condition due to SSRI treatment can occur. An improved treatment result is an overall improvement assessed over the whole group. Improvement can be solely due to an overall reduction in frequency or intensity of side effects. It is also possible that doses can be increased or the dosing regime can be stepped up faster thanks to less troublesome side effects in the group and consequently an earlier onset of recovery or better remission of the disease.

A disorder, which is responsive to treatment with an SSRI, is defined to be a disorder, which is, according to recommendations in professional literature and drug formularies, known to respond with at least partial remission of the symptoms to a treatment with an SSRI. In most countries such recommendations are subject to governmental regulations, allowing and restricting the mention of medical indications in package inserts. Other sources are drug formularies of health management organisations. Before approval by governmental agencies certain recommendations can also be recognised by publications of confirmed treatment results in peer reviewed medical journals. Such collective body of information defines what is understood here to be a disorder which is responsive to treatment with an SSRI. Being responsive to SSRI treatment does not exclude that the disorder in an individual patient can resist treatment with an SSRI, as long as a substantial portion of persons having the disorder respond with improvement to the SSRI treatment.

In the section describing the background of the invention examples of SSRI responsive disorders were listed. Known disorders which are responsive to treatment with an SSRI are, for example, major depressive disorder, dysthymia, premenstrual dysphoric disorder, panic disorder, obsessive compulsive disorder, social phobia, post-traumatic stress disorder, generalised anxiety disorder, obesity, bulimia nervosa, alcoholism, trichotillomania, paraphilia and related disorders, borderline personality disorder, smoking cessation and drug abuse.

The technical field defines an SSRI as a drug which inhibits the reuptake of serotonin in nerve terminals in the brain more effectively than the reuptake of noradrenaline and dopamine. Such drugs are treated as a group with common properties due to this mechanism of action and this selectivity. Known drugs specifically named as SSRI are fluoxetine, fluvoxamine, citalopram, cericlamine, femoxetine, sertraline, paroxetine, ifoxetine, cyanodothiepin and litoxetine, of which fluoxetine, fluvoxamine, citalopram, sertraline and paroxetine are the ones with which most experience is obtained and which are preferred indicators for defining the SSRI responsive disorders for which the method according to this invention can be applied (Hermann, Canadian J Clin Pharmacol 7: 91-95, 2000; Modell et al., Clin Pharm & Ther 61: 476-487, 1997; Lucki et al., Neurosci biobehav. Rev 18: 85-95, 1994).

The method to obtain an improved treatment result comprises:
a) Diagnosing a person for having a disorder, which responds to treatment with an SSRI.
b) Genotyping the person to determine whether the person is a homozygous carrier of 102C alleles of the gene for the 5-HT$_{2A}$-receptor.
c) Adapt the further treatment of the person differentially depending on the presence or absence of the said sequence in the person.

This method does not necessarily prescribe these steps in the indicated sequence. In practice an SSRI treatment can be started before the steps to confirm the suitability of the treatment can be started. The genotyping serves to decide on timely adapting the further treatment when the person is found to fall into the genotype category homozygous 102 C/C for the 5-HT$_{2A}$ receptor.

For further treatment the category (A) of persons of the homozygous 102 C/C genotype is to be differentiated from the category (B) of persons of the 102 T/C and T/T genotypes.

Adapting the further treatment of the person differentially depending on the presence or absence of the said sequence in the person is a measure which should consist of the following measures:

For category A the further treatment should be either
1) administering a below average dose of an SSRI, or
2) co-administering a drug treatment which diminishes SSRI side effects, or
3) instructing and helping the person to accept the inconveniences of the side effects, or
4) starting or switching to an alternative, non-SSRI treatment.

For category B the further treatment should be either
1) starting or continuing as if no information on said genotype is available
2) a more aggressive approach in the treatment with an SSRI, in the case that an SSRI-treatment is or is to be selected, by administering the person a higher dose or stepping up the dose in a more progressive regime than would be done if no info information on the genotype was known.

The adaptation for category A persons amounts to selecting a therapy diminishing the risk for side effects of an SSRI treatment for the person. Preferred is to apply a therapy which is recognised to be an alternative for a treatment with an SSRI.

When the genotyping is performed, or the result is known, after start of an SSRI treatment and the treated person is found to have the 102 C/C genotype and side effects are experienced with SSRI treatment, then, because there is a high probability that the person will eventually discontinue SSRI treatment, the person's burden can be decreased by applying an alternative treatment. As a result the time required to achieve an improvement can be reduced by applying an alternative therapy, since the probability of eventually discontinuing treatment with the SSRI is high in a person with the 102 C/C genotype.

The selection of a therapy which is recognised to be an alternative for a treatment with an SSRI is defined by reference to the general knowledge in this medical field. It is standard practise to diagnose a disorder in a person and select a therapy which is indicated for the disorder. An example of a reference manual for diagnostic methods is the Diagnostic and Statistical Manual of Mental Disorders 4th edition (DSM-IV) published by the American Psychiatric Association, Washington, D.C. (1994). Supplementary to this the SSRI responsive disorders can be identified objectively on the basis of recommendations in government approved labels, by health management organisations and in confirmed reports of positive treatment results in peer reviewed medical literature, it is similarly known to the skilled person that alternative non-SSRI treatments are available. Examples of non-SSRI anti-depressant treatments are, for example, treatments with drugs, which act by blocking the reuptake of norepinephrine, or by blocking $\alpha_2$ adrenergic or serotonin receptors. Specific alternative antidepressants are venlafaxine, mirtazapine, nefazodone, doxepine and imipramine, of which mirtazapine, of course in an amount effective to treat depression, is preferred for the indication of major depression. Alternative treatments for prescribing an SSRI can also be non-drug treatments, such as behavioural therapies or electroconvulsive shock treatment. Benzodiazepine-like anxiolytic compounds can be used for anxiety disorders. A therapy diminishing the risk for side effects of an SSRI treatment can also be a treatment with a below average dose of the SSRI or providing an additional treatment to prevent side effects.

The amount of mirtazapine effective to treat depression will, of course, vary and is ultimately at the discretion of the medical practitioner. The factors to be considered include the route of administration and nature of the formulation, the body weight, age, and general state health, and severity of the depression. Unless otherwise stated, all weights of active ingredients referred to herein are calculated in terms of the active drug per se. In general, a suitable dose of mirtazapine for administration to a human will be in the range of 5 to 100 mg per day. In one embodiment, the suitable dosage range for administration of mirtazapine to a human may be 15 to 45 mg per day. The desired dose may be presented as two, three, four, five, or more sub-doses administered at appropriate intervals throughout the day. These sub-doses may be administered in unit dosage forms, for example, containing 15 mg, 30 mg, or 45 mg, or any unit dosage useful to allow multiple dosing in a single day.

No clear explanation of the effect of the invented method can be given. It may be relevant that the $5\text{-HT}_{2A}$ receptor is located on the membrane of postsynaptic neurones and interacts with serotonin molecules in the synaptic cleft. It has been theorised that the side effects of selective serotonin reuptake inhibitors such as paroxetine are mediated through this receptor. Genetic variants of the $5\text{-HT}_{2A}$ receptor may alter the binding of serotonin to the receptor, or alter the signal that the activated receptor transmits to the postsynaptic neuron in the brain. $5\text{-HT}_{2A}$ receptors are also located on smooth muscle cells in the gastrointestinal tract and blood vessels. Carriers of the C/C genotype may have side effects such as gastrointestinal upset and dizziness after paroxetine due to altered reaction of smooth muscle cells to serotonin stimulation of $5\text{-HT}_{2A}$ receptors. $5\text{-HT}_{2A}$ receptors are also thought to be important in level of alertness and sleep. Insomnia and agitation experienced by subjects carrying the C/C genotype may have been due to altered function of $5\text{-HT}_{2A}$ receptors regulating alertness and sleep.

The $5\text{-HT}_{2A}$ receptor 102 T/C polymorphism is a "silent" genetic marker that does not result in an amino acid substitution in the functional protein. Without implying any restriction on the claims and use of the invention it can be suggested that the effect we have found on intolerance to an SSRI of 102C/C genotype patients can be due to another nearby variant in the gene that directly affects its function. The 102 T/C polymorphism and the functional variant are said to be in "linkage disequilibrium", meaning that the 102 T/C variant is a marker for a polymorphism in close proximity that affects the receptor function. However, this in no way diminishes the importance of the 102 T/C polymorphism as a predictor of side effects to an SSRI, as found in the present invention. Many existing medical tests are useful markers for an underlying biological process. For example, the erythrocyte sedimentation rate (ESR) is a commonly used marker for an inflammatory reaction, even though it does not define the exact nature of the underlying inflammatory disease.

To screen patients for the gene, genomic DNA can be extracted from EDTA-treated whole blood using, for example, the Puregene DNA extraction kit (available from Gentra Systems). Genotypes can be determined using restriction isotyping (restriction enzyme isoform genotyping) following in general the method of Du et al. (Am J Med Genet. 2000 Feb. 7;96(1):56-60). Thus, the 5-HT2A gene presence in the extract can be amplified by about 30 cycles of polymerase chain reaction primed by the primers 5-HT2AR-1 (agcagaaactataacctgtt) (SEQ ID NO: 1) and 5-HT2AR-2 (caagtgacatcaggaaatag) (SEQ ID NO: 2) followed by a final extension step. This PCR product can be digested with a specific restriction enzyme cutting 5-HT2A polynucleotides as a consequence of recognition of the 102 C/T difference such that one allele remains undigested, yielding the full 410 base pair fragment, while the other allele is cut into two fragments. The digested samples can then be separated and determined by gel electrophoresis.

EXAMPLE

Treatment Protocol 122 patients with major depression were treated for 8 weeks with paroxetine. All subjects were 65 years of age or older and had been free of 10 major medical problems for at least 3 months. At screening, all met DSM-IV criteria for major depression (single or recurrent), had Mini Mental State Examination scores above the 25th percentile for their age, and had a Hamilton Depression Rating Scale 17-item (HDRS-17) score of at least 18. Patients were excluded for clinically significant laboratory abnormalities, drug or alcohol abuse, psychosis, recent suicide attempt, and psychiatric conditions other than major depression, or treatment with antidepressant medications within 7 days of commencing the study.

Initial treatment was with 20 mg of paroxetine (two 10 mg capsules) given each evening. On day 14, doses were increased to 30 mg of paroxetine once daily. At days 28 and 42, dose increases to 40 mg of paroxetine were allowed if the patient had a Clinical Global Impression (CGI) improvement score of greater than 2. Patients were seen in clinic at days 7, 14, 21, 28, 42, and 56 of treatment.

Genetic Analysis

Genomic DNA was extracted from EDTA-treated whole blood using the Puregene DNA extraction kit (Gentra Systems). Genotype for the 102 T/C DNA sequence polymorphism in the $5\text{-HT}_{2A}$ receptor gene was determined using the method of Du et al. (Am J Med Genet. 2000 Feb. 7;96(1):56-60). Specifically, 2.5 μL 10× PCR buffer (Applied Biosystems); 0.25 µL of 10 mmol/L dNTP (Amersham); 0.05 µL of primer 5-HT2AR-1 (SEQ ID NO. 1: agcagaaactataacctgtt) at 100 pmol/µL; 0.05 µL of primer 5-HT2AR-2 (SEQ ID NO. 2: caagtgacatcaggaaatag) at 100 pmol/.mu.L; and 0.1 µL of Taq polymerase at 5 U/µL, (Applied Biosystems) are mixed with 1 µL of genomic DNA at 0.23 to 1.1 µg/µL in a total volume of 25 µl. After an initial 5 minute denaturing step at 95° C., the reaction mixture goes through 30 cycles of polymerase chain reaction (PCR) (95° C. for 1 min, 52° C. for 30 sec, and 72° C. for 1 min), followed by final extension at 72° C. for 10 minutes. 8 µL of this PCR product is digested with 0.5 µL of the Msp I restriction enzyme (20 U/µL, NEB), 1.5 µL of 10× buffer 2, and 5 µL of water for 4 hours at 37° C. The digested samples are then separated on a 2% agarose gel in a field of 4 V/cm. The T allele remains undigested, yielding the full 410 base pair fragment, while the C allele is cut into 162 and 248 bp fragments.

Outcome Measures

Discontinuations were classified as due to any event, and as due to an adverse event. Severity of adverse events were obtained by clinician ratings that were standardised for drug exposure time and dosage. Plasma drug levels were obtained at day 28. Body weight was determined at baseline and at each subsequent visit. Actual medication taken Was determined by counting the number of tablets remaining at each clinic visit. Dosing compliance was determined by as total number of medication doses taken divided by total number of capsules given.

Results

I. Genotypes Divided Two Ways (C/C Versus T/C and T/T Groups) All Subjects

The frequencies of genotypes were:
Paroxetine C/C=41 patients (33.6%)
Paroxetine T carriers (T/C and T/T)=81 patients (66.4%)
Over the 8 week study, paroxetine C/C patients had:
Greater severity of adverse events due to study drug (p=0.03)
Lower final daily dose (p=0.08)
Lower dosing compliance (p=0.06)
Lower plasma levels at day 28 (p=0.056)
More subjects discontinuing early (p=0.049), and more subjects discontinuing early due to adverse events (46.3% for C/C genotype, 16% for other subjects; p=0.001)

(p values above are from F tests comparing mean values, or from Cochran-Mantel-Haenszel statistics comparing proportions. These values indicate statistically significant (p<0.05), or marginally statistically significant (p<0.10) differences).

The lower final daily dose, lower dosing compliance, and lower plasma levels were likely due to more severe side effects in patients with. C/C genotype, resulting in decreased ability to take doses of paroxetine that were well tolerated by other patients with the T/C and T/T genotypes.

Survival analyses for dropouts showed that patients with C/C genotype had significantly greater likelihood of dropping out of the study than did other subjects at every assessment point. Statistics below are p values from Kaplan-Meier survival analyses. That is, at day 7 the probability that the increased dropout rate of patients with the C/C genotype was due to random factors was only 0.001, or one in one-thousand. This indicates that these results are highly reliable.

|        | All causes | Adverse events |
|--------|------------|----------------|
| Day 7  | .003       | .001           |
| Day 14 | .005       | .001           |
| Day 21 | .009       | .001           |
| Day 28 | .009       | .001           |
| Day 42 | .014       | .001           |
| Day 49 | .008       | .001           |

Caucasian Subjects

There were no significant differences between the two genotype groups in the frequency of ethnic minorities. However, because of possible effects of genetic background, data for Caucasians were analysed separately.
Paroxetine C/C=36 patients (33.0%)
Paroxetine T carriers (T/C and T/T)=73 patients (67.0%)
There were no significant differences between C/C and T/- groups in age, gender, ethnicity, baseline body weight, cognition, or severity of depression at baseline.
Paroxetine C/C subjects had:
Greater severity of side effects due to study drug (p=0.051)
More discontinuations due to any cause (C/C=63.9%; T/T and T/C=45.2%) p=0.068
More discontinuations due to adverse events (C/C 47.2%; T/T and T/C=16.4%) p<0.001
Survival Analyses showed C/C subjects had a significantly greater probability of discontinuation:

|        | All causes | Adverse events |
|--------|------------|----------------|
| Day 7  | .006       | .001           |
| Day 14 | .010       | .001           |
| Day 21 | .019       | .002           |
| Day 28 | .019       | .002           |
| Day 42 | .028       | .004           |
| Day 49 | .016       | .001           |

I. Genotypes Divided Three Ways (C/C Versus T/C Versus T/T) AU Subjects

The data were also analysed with subjects divided into three genotype groups.
41 subjects with C/C genotype (33.6%)
63 subjects with C/T genotype (51.6%)
18 subjects with T/T genotype (14.8%)
122 total No significant differences were found between genotype groups in age, gender, ethnic origin, or body weight for either drug. No significant differences were found among genotype groups in final daily dose achieved, dosing compliance, plasma drug concentrations at day 28. There were no differences in average daily dose at each visit, except at day 7, when C/C carriers took less medication than the other two genotype groups. This was probably due to intolerance of the medication in C/C carriers. The probability of discontinuation due to an adverse event was linearly related to increasing dosage of the C allele (C/C=3, C/T=2, T/T=1). That is the greater the number of C alleles, the higher the probability of discontinuation.

|         | All causes | Adverse event |
|---------|------------|---------------|
| Day 7:  | NS         | .016          |
| Day 14: | .048       | .010          |
| Day 21: | .047       | .009          |

-continued

|  | All causes | Adverse event |
| --- | --- | --- |
| Day 28: | .047 | .009 |
| Day 42: | NS | .020 |
| Day 49: | .052 | .009 |

(NS = no significant difference)

Caucasian Subjects, 3-Way Classification
36 subjects with C/C genotype (33.0%)
56 subjects with C/T genotype (56.0%)
17 subjects with T/T genotype (15.6%)

There were no significant differences among the 3 genotype groups (C/C vs. T/C vs. T/T) in the frequency of ethnic, minorities. However, because of possible effects of genetic background, data for Caucasians were analysed separately.

Among Caucasian subjects, there were no significant differences among the genotype groups in age, gender, body weight, final daily dose, or overall dosing compliance.

At day 7, subjects with the C/C genotype took significantly less paroxetine than subjects with C/T and T/T genotypes (p=0.035). Survival analyses did not show a difference among the 3 genotype groups in discontinuations due to any cause. However, discontinuations due to adverse events showed:

| Day 7: | 0.039 |
| --- | --- |
| Day 14: | 0.022 |
| Day 21: | 0.019 |
| Day 28: | 0.019 |
| Day 42: | 0.051 |
| Day 49: | 0.020 |

Results for Mirtazapine 122 additional patients with similar characteristics to those treated with paroxetine received mirtazapine treatment under the same conditions. Initial treatment was with 15 mg mirtazapine (one active capsule and one placebo capsule) given each evening. On day 14, doses were increased to 30 mg once daily. At days 28 and 42, dose increases to 45 mg of mirtazapine were allowed if the patient had a Clinical Global Impression (CGI) improvement score of greater than 2. All patients Were genotype for the 102 T/C polymorphism using the method described above. Results showed that mirtazapine-treated patients with the C/C genotype had no greater probability of discontinuing treatment due to side effects than did other subjects, and no greater severity of side effects than others. These results are in marked contrast to those obtained with paroxetine treatment. Mirtazapine treated subjects also showed statistically significant improvement in mood (decreased depression) as measured by the Hamilton Depression Rating Scale over the 8 week treatment period. This result was not affected by the 102 T/C polymorphism.

Conclusion

These results illustrate the major effect of the 5-HT$_{2A}$ receptor 102 T/C polymorphism on adverse events in patients treated with paroxetine. Subjects of the C/C genotype had a significantly higher probability of discontinuation due to adverse events than did other subjects at every evaluation point during the 8 week study. Subjects of the C/C genotype also took significantly less medication taken at day 7, and showed trends toward a lower final daily dose, and lower dosing compliance. This suggests that the subjects with C/C found paroxetine unpleasant due to side effects. The side effects experienced by subjects with the C/C genotype were more severe than those experienced by other subjects. Typical side effects experienced by C/C carriers who dropped out of the study included dizziness, somnolence, insomnia, agitation, trouble concentrating, vomiting, nausea, and diarrhea.

The association between the 102 T/C polymorphism and discontinuations due to adverse events is present in both the full sample as well as in the subsample of Caucasian subjects. This indicates that the result is not due to population stratification, meaning the result is not due to including subjects of different ethnic backgrounds in the study. The result is robust regardless of whether the data are analysed as C/C genotype vs. T/C and T/T or with three genotype levels (C/C, T/C, T/T).

The comparison study with mirtazapine showed that the 102 T/C polymorphism does not affect severity of side effects or dropouts due to side effects in depressed patients treated with this medication. Patients treated with mirtazapine, including those with C/C genotype, showed a statistically significant improvement in mood at the end of the 8 week study. This indicates that therapy with mirtazapine is an effective and safe alternative to SSRI treatment in patients who have the C/C genotype.

The invention claimed is:

1. A method for determining an increased risk for side effects of selective serotonin reuptake inhibitor (SSRI) treatment in a human subject, the method comprising:
   a) genotyping a nucleic acid sample from the subject to detect the presence of a 102 C/C DNA sequence in the subject's 5-$HT_{2A}$ receptor gene; and
   b) determining from said genotyping an increased risk for side effects of a selective serotonin reuptake inhibitor (SSRI) treatment in the subject.

2. The method according to claim 1, wherein the subject suffers from depression.

3. A method to improve a treatment of a selective serotonin reuptake inhibitor (SSRI) responsive disorder in a subject, comprising:
   a) genotyping a nucleic acid sample from the subject to detect the presence or absence of the 102 C/C DNA sequence in the subject's 5-$HT_{2A}$ receptor gene;
   b) determining from said genotyping whether said subject has an increased risk for side effects of a selective serotonin reuptake inhibitor (SSRI) treatment; and
   c) adapting the treatment differentially depending on the presence or absence of said sequence in the subject.

4. The method according to claim 3, wherein the 102 C/C DNA sequence is found in the subject's 5-$HT_{2A}$ receptor gene and the subject is treated with a psychoactive pharmaceutical composition free of selective serotonin reuptake inhibitors.

5. The method according to claim 4, wherein the SSRI responsive disorder is depression and the treatment is adapted by administering mirtazapine in an amount effective to treat depression.

6. The method of claim 1, wherein the subject is 65 years of age or older.

7. The method according to claim 1, wherein said genotyping is by a method selected from the group consisting of: restriction isotyping, polymerase chain reaction, gel electrophoresis, hybridization, oligotyping, and nucleic acid sequencing.

8. The method of claim 1, wherein said genotyping comprises analyzing a sample of whole blood from said subject.

9. The method according to claim 1, wherein said side effects are selected from the group consisting of: headache, dizziness, agitation, trouble concentrating, gastrointestinal disturbance, nausea, vomiting, diarrhea, appetite inhibition, sleep disturbance, somnolence, insomnia, and disturbance of sexual function.

10. The method according to claim 1, wherein said side effect is premature drug-related discontinuation of a SSRI treatment.

11. The method according to claim 1, further comprising adapting a treatment differentially depending on said subject's 5-$HT_{2A}$ receptor genotype.

12. The method according to claim 11, wherein said treatment comprises a psychoactive pharmaceutical composition free of selective serotonin reuptake inhibitors.

13. The method according to claim 12, wherein said composition free of selective serotonin reuptake inhibitors comprises mirtazapine.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1
agcagaaact ataacctgtt                                            20

<210> SEQ ID NO 2
<211> LENGTH: 20
<212> TYPE: DNA
<213> ORGANISM: Homo sapiens

<400> SEQUENCE: 2
caagtgacat caggaaatag                                            20